US010178979B2

(12) United States Patent
Majewski et al.

(10) Patent No.: US 10,178,979 B2
(45) Date of Patent: *Jan. 15, 2019

(54) ENDORECTAL PROSTATE PROBE COMPOSED OF A COMBINED MINI GAMMA CAMERA AND ULTRASOUND SENSOR

(71) Applicant: West Virginia University, Morgantown, WV (US)

(72) Inventors: Stanislaw Majewski, Morgantown, WV (US); Gary Marano, Morgantown, WV (US); Alexander Stolin, Morgantown, WV (US); James Proffitt, Newport News, VA (US)

(73) Assignee: West Virginia University, Morgantown, WV (US)

( * ) Notice: Subject to any disclaimer, the term of this patent is extended or adjusted under 35 U.S.C. 154(b) by 22 days.

This patent is subject to a terminal disclaimer.

(21) Appl. No.: 15/002,735

(22) Filed: Jan. 21, 2016

(65) Prior Publication Data

US 2016/0278723 A1 Sep. 29, 2016

Related U.S. Application Data

(62) Division of application No. 13/804,606, filed on Mar. 14, 2013, now Pat. No. 9,271,686.

(51) Int. Cl.
*A61B 6/00* (2006.01)
*A61B 6/04* (2006.01)
(Continued)

(52) U.S. Cl.
CPC .......... *A61B 6/4417* (2013.01); *A61B 5/4381* (2013.01); *A61B 6/0407* (2013.01);
(Continued)

(58) Field of Classification Search
CPC ... A61B 6/4417; A61B 6/4429; A61B 8/5261; A61B 8/4254; A61B 6/54; A61B 8/54;
(Continued)

(56) References Cited

U.S. PATENT DOCUMENTS 4,781,198 A 11/1988 Kanabrocki
4,995,396 A 2/1991 Inaba et al.
(Continued)

FOREIGN PATENT DOCUMENTS

WO 2004042546 5/2004
WO 2006123119 11/2006
(Continued)

OTHER PUBLICATIONS

Egorov, Vladimir et al., "Prostate Mechanical Imaging: 3-D Image Composition and Feature Calculations," IEEE Trans Med Imaging, Oct. 2006; 25(10): 1329-1340. doi:10.1109/TMI.2006.880667.
(Continued)

*Primary Examiner* — Sanjay Cattungal
(74) *Attorney, Agent, or Firm* — Buchanan Ingersoll & Rooney PC; Craig G. Cochenour, Esq.

(57) ABSTRACT

A dual modality probe is disclosed having both a gamma probe sensor and an ultrasound sensor. A dual imaging system is provided having the probe and at least one external gamma imaging detector and a data acquisition computer system for collecting data simultaneously from the gamma probe sensor, the gamma imaging detector, and the ultrasound sensor of the probe. A method for evaluating a target organ of a patient utilizing the probe and imaging system, and performing a biopsy of the organ is disclosed.

12 Claims, 12 Drawing Sheets

(51) Int. Cl.
*A61B 8/12* (2006.01)
*A61B 8/00* (2006.01)
*A61B 5/00* (2006.01)
*A61B 8/08* (2006.01)
*A61B 10/02* (2006.01)

(52) U.S. Cl.
CPC ............ *A61B 6/4429* (2013.01); *A61B 6/481* (2013.01); *A61B 6/5247* (2013.01); *A61B 6/54* (2013.01); *A61B 8/12* (2013.01); *A61B 8/4245* (2013.01); *A61B 8/4254* (2013.01); *A61B 8/4416* (2013.01); *A61B 8/4444* (2013.01); *A61B 8/5261* (2013.01); *A61B 8/54* (2013.01); *A61B 10/0241* (2013.01)

(58) Field of Classification Search
CPC ... A61B 5/4381; A61B 10/0241; A61B 6/481; A61B 6/5247; A61B 8/4416; A61B 8/4444; A61B 8/4245; A61B 8/12; A61B 6/0407
USPC ................................................ 600/436–469
See application file for complete search history.

(56) References Cited

U.S. PATENT DOCUMENTS

| | | | |
|---|---|---|---|
| 5,014,708 | A | 5/1991 | Hayashi et al. |
| 5,170,055 | A | 12/1992 | Carroll et al. |
| 5,776,062 | A | 7/1998 | Nields |
| 5,873,828 | A | 2/1999 | Fujio et al. |
| 6,288,397 | B1 | 9/2001 | Maor |
| 6,389,098 | B1 | 5/2002 | Keppel et al. |
| 6,512,943 | B1 | 1/2003 | Kelcz |
| 6,546,279 | B1 | 4/2003 | Bova et al. |
| 6,951,542 | B2 | 10/2005 | Greppi et al. |
| 7,653,427 | B2 | 1/2010 | Essner et al. |
| 7,711,409 | B2 | 5/2010 | Keppel et al. |
| 7,858,944 | B2 | 12/2010 | Majewski et al. |
| 7,894,876 | B2 | 2/2011 | von Rueckmann et al. |
| 7,919,756 | B2 | 4/2011 | Beekman |
| 2004/0162479 | A1 | 8/2004 | Yamamoto et al. |
| 2005/0082487 | A1 | 4/2005 | Amano |
| 2005/0207530 | A1 | 9/2005 | Inoue et al. |
| 2005/0213705 | A1 | 9/2005 | Hoffman |
| 2006/0106306 | A1* | 5/2006 | Essner ............... A61B 8/0833 600/436 |
| 2007/0282221 | A1 | 12/2007 | Wang et al. |
| 2009/0112086 | A1 | 4/2009 | Melman |
| 2009/0270760 | A1 | 10/2009 | Leimbach et al. |
| 2010/0198063 | A1 | 8/2010 | Huber et al. |
| 2011/0082369 | A1 | 4/2011 | Mohr et al. |
| 2011/0201965 | A1 | 8/2011 | Hibner et al. |
| 2013/0137964 | A1 | 5/2013 | Schellenberg |
| 2013/0172739 | A1* | 7/2013 | Paladini ............... A61B 6/4258 600/436 |

FOREIGN PATENT DOCUMENTS

| | | |
|---|---|---|
| WO | 2009009223 | 1/2009 |
| WO | 2009153229 | 12/2009 |

OTHER PUBLICATIONS

Trabulsi, Edouard J. et al., "Enhanced Transrectal Ultrasound Modalities in the Diagnosis of Prostate Cancer," doi:10.1016/j.urology.2010.05.022.
Aigner, Friedrich, et al., "Status of Transrectal Ultrasound Imaging of the Prostate," Journal of Endourology; May 2010; 24(5); 685-691.
Huber, J.S., et al., "Initial Results of a Positron Tomograph for Prostate Imaging," TNS 53, 2006, pp. 2653-2659.
Turkington, Timothy G., et al., "PET Prostate Imaging with Small Planar Detectors," Medical Imaging Conference Record, 2004 IEEE vol. 5, Oct. 16-22, 2004, pp. 2806-2809.
Wu, H., et al., "Micro Insert: A Prototype Full-Ring PET Device for Improving the Image Resolution of a Small-Animal PET Scanner," The Journal of Nuclear Medicine, vol. 49, No. 10, Oct. 2008.
Tai, Y-C, "Virtual-pinhole PET," J Nucl. Med. 2008; 49:471-479.
Zhou, Jian, et al. "Theoretical Analysis and Simulation Study of a High-Resolution Zoom-In PET System," Phys. Med. Biol. 54 (2009), pp. 5193-5208.
Huh, Sam S. et al., "Investigation of an Internal PET Probe for Prostate Imaging," Nuclear Instruments and Methods in Physics Research, Section A, 2007, vol. 579, No. 1, pp. 339-343.
Huber, J.S., et al., "Characterization of a PET Camera Optimized for Prostate Imaging," 2005 IEEE Nuclear Science Symposium Conference Record, vols. 1-5, 1:1556-9.
Huber, J.S., et al., "Dual-Modality PET/Ultrasound Imaging of the Prostate," http://repositories.cdlib.org/lbnl/LBNL-59114.
Levin, C., "New Photon Sensor Technologies for PET in Prostate-Specific Imaging Configurations," presented at the Topical Symposium on E1Advanced Molecular Imaging Techniques in the Detection, Diagnosis, Therapy, and Follow-Up of Prostate Cancer, Dec. 6-7, 2005, Rome, Italy, http://www.iss.infn.it/congresso/prnstate/presentationsauthor.htm.
Moses, W., "Dedicated PET Instrumentation for Prostate Imaging," presented at the Topical Symposium on Advanced Molecular Imaging Techniques in the Detection, Diagnosis, Therapy, and Follow-Up of Prostate Cancer, Dec. 6-7, 2005, Rome, Italy, http://www.iss.infn.it/congresso/prostate/presentations author.htm.
Mullani, et al., "First-Pass 18F-FDG PET of Blood Flow," The Journal of Nuclear Medicine, vol. 49, No. 4, Apr. 2008.
Greenlee, R.T. et al., "Cancer Statistics", 2001, CA Cancer J. Clin., 2001, vol. 51, pp. 15-36.
Ward, J.F. et al., "Radical Prostatectomy for Clinically Advanced (cT3) Prostate Cancer Since the Adent of Protate-Specific Antigen Testing: 15-year Outcome", BJU Int., 2005, vol. 95, pp. 751-756.
Kupelian, P. et al., Year of Treatment as Independent Predictor of Relapse-Fee Survival in Patients With Localized Prostate Cancer Treated with Definitive Radiotherapy in the PSA Era, Int. J Radiat Oncol Biol Phys., 2005 vol. 63, pp. 795-799.

* cited by examiner

ENDORECTAL PROSTATE PROBE COMPOSED OF A COMBINED MINI GAMMA CAMERA AND ULTRASOUND SENSOR

CROSS-REFERENCE TO RELATED APPLICATION

This utility patent application claims the benefit of co-pending U.S. patent application Ser. No. 13/804,606, filed on Mar. 14, 2013. The entire contents of U.S. patent application Ser. No. 13/804,606 are incorporated by reference into this utility patent application as if fully rewritten herein.

BACKGROUND OF THE INVENTION

Field of the Invention

The present invention relates to a device and method for performing hybrid imaging of organs and tumors. More particularly, an endorectal probe is provided for imaging of a prostate gland wherein the probe (device) has combined gamma camera and ultrasound imaging modalities.

Description of the Background Art

There are >200,000 new cases and nearly 30,000 deaths each year from prostate cancer (PCa) Prostate-specific antigen (PSA) testing has allowed early detection of impalpable PCa. Early detection has lowered the incidence of advanced disease with extracapsular extension and the subsequent early treatment appears to improve survival rate. After anomalous PSA results, the patient undergoes biopsy, and if the biopsy is positive, the patient undergoes surgery. The main objective of surgery is to remove the cancer at lowest functional cost, i.e. preserving continence and sexual function. The stage of the cancer decides the limits of the resection, and the larger the tumor the wider the excision needed, with radical prostatectomy as the limit of standard treatment. An accurate localization of the tumor and assessment of its size has two important advantages: it can direct the biopsy and can assist with the surgery. Biopsy results may be negative despite the presence of cancer due to sampling error. Prostate cancer is the only human cancer that does not have a standard method to image the primary tumor. The "blind" biopsy typically performed today under ultrasound (US) guidance results in high false negative diagnosis with many missed cancers. Accurate localization of the tumor, within the prostate and pelvic region, will better enable a tumor-free margin. Such accurate assessment today is not available with conventional imaging techniques [ultrasound (US), computed tomography (CT), magnetic resonance imaging and PET]. Standard PET scanners have spatial resolution inadequate to meet the clinical needs of prostate imaging—particularly when using specific, targeted imaging agents.

The diagnosis of prostate cancer is commonly based on a combination of digital rectal examination (DRE), serum prostate specific antigen (PSA) value, and transrectal ultrasound (TRUS) guided prostate biopsy findings. Conventional blind "biopsy" procedures under Tissue Differentiating Ultrasound are able to visualize only the structure and the margins of an organ, and thus do not provide differentiation between a cancerous tissue and healthy tissue.

Prostate cancer is the only human cancer that does not have a standard reliable method of imaging of the primary tumor. Functionally blind biopsy typically performed today under transrectal ultrasound guidance results in high false negative diagnoses with many missed cancers. Accurate localization of the tumor, within the prostate and pelvic region, will allow definition of a tumor-free margin. Such accurate assessment is generally not available in the present state of the art, with the conventional imaging techniques available to urologists.

Thus, those persons skilled in the art appreciate that prostate cancer is difficult to visualize in its early stage using current imaging technology. Conventional imaging modalities, such as ultrasound, CT (computed tomography) scan, and MRI (magnetic resonance imaging), can be used for the anatomic evaluation of prostate cancer. However, visible anatomic changes are not always present in early stages of the disease, making the use of current imaging modalities difficult in early detection of prostate cancer sites. The key problem with conventional guiding systems during prostate biopsy is that they are based on symmetrical anatomical sampling of the prostate, and not on the location of the cancer. The main challenge continues to be the inability to visualize the cancer in its early stages using current imaging technology.

Recently, Hybridyne imaging technologies introduced to the market (FDA approval was obtained in Spring of 2010) a prostate mini gamma probe based on Cadmium Zinc Telluride (CZT) Technology.

U.S. Pat. No. 7,919,756 "Gamma image detection device" discloses a detection device comprising first and second gamma cameras. No ultrasound device is disclosed.

U.S. Pat. No. 7,711,409 "Opposed view and dual head detector apparatus for diagnosis and biopsy with image processing methods" discloses opposed gamma cameras. No ultrasound device is disclosed.

International Published Patent Application No. WO 2009/153229 "Improved gamma-ray imaging device for precise location of irradiating sources in space" discloses a dual modality method using a gamma ray imaging device and an auxiliary visible-light camera. No ultrasound device is disclosed.

U.S. Published Application No. US 2009/0112086 "Prostate imaging" discloses an insertable polymer probe, detectable by a gamma camera and an ultrasound device, where neither the gamma camera nor the ultrasound device is inserted into the patient.

International Published Patent Application no. WO 2009/009223 "Co-registration for dual PET-transrectal ultrasound prostate imaging" discloses a dual modality method using a PET scanning device and an ultrasound device. No gamma camera is disclosed.

International Published Patent Application No. WO 2006/123119 "Imaging device and method" discloses a dual modality method using a visible light device and a gamma ray imager. No ultrasound device is disclosed.

U.S. Published Patent Application No. US 2005/0213705 "Methods and systems for multi-modal imaging" discloses neither a gamma camera, nor an ultrasound device. Patient examination is conducted in a gantry.

U.S. Published Patent Application No. US 2005/0207530 "Medical imaging diagnosis apparatus" discloses a dual modality method using an X-ray CT scanner and a PET scanner. No gamma camera or ultrasound device is disclosed.

U.S. Published Patent Application No. US 2005/0082487 "Diagnostic imaging device for medical use" discloses a dual modality method using an X-ray CT scanner and a PET scanner. No gamma camera or ultrasound device is disclosed.

International Published Patent Application No. WO 2004/042546 "Apparatus and methods for imaging and attenuation correction" discloses a system comprising a gamma imager, an ultrasound imager, and a computerized system for reconstructing and superimposing images. The gamma imager and the ultrasound imager are operated external to the patient.

U.S. Pat. No. 6,389,098 "Dual mode stereotactic localization method and application" discloses a device configured to obtain both a X-ray mammographic image and a gamma mammographic image. X-ray imaging and gamma imaging are disclosed, but ultrasound imaging is not disclosed.

U.S. Pat. No. 6,288,397 "Dual detector gamma camera system" discloses two gamma detectors arranged in a L-shaped configuration. No ultrasound imaging is disclosed.

U.S. Pat. No. 7,711,409 "Opposed view and dual head detector apparatus for diagnosis and biopsy with image processing methods" discloses opposed gamma cameras for guiding a biopsy needle, but discloses no ultrasound imaging components.

U.S. Pat. No. 7,653,427 "Method and instrument for minimally invasive sentinel lymph node location and biopsy" discloses a radiation detector coupled with an ultrasound probe, for locating the position of a tagged tissue, and placement of a biopsy device.

U.S. Pat. No. 6,951,542 "Method and apparatus for ultrasound imaging of a biopsy needle or the like during an ultrasound imaging examination" discloses method including imaging and injection of contrast agents for placement of a biopsy device.

U.S. Pat. No. 6,546,279 "Computer controlled guidance of a biopsy needle" discloses a system for guiding a biopsy needle using one or more of computed tomography imaging, magnetic resonance, fluoroscopic imaging, or 3-D ultrasound imaging.

U.S. Pat. No. 6,512,943 "Combined ultrasound-radionuclide device for percutaneous ultrasound-guided biopsy and method of use" discloses a system and apparatus for performing tissue biopsy. An ultrasound imager and a "radionuclide detectors" are used, external to a patient, to locate "nuclear medicine tracer uptake" in the patient and generate superimposed images of an area of interest.

U.S. Pat. No. 5,776,062 "Enhanced breast imaging/biopsy system employing targeted ultrasound" discloses a system using X-ray imaging and ultrasound, external to a patient, to provide 3-D imaging of an area of interest for use with a biopsy procedure.

U.S. Pat. No. 5,170,055 "Radiation detecting biopsy probe" discloses a handheld biopsy probe that is guided by means of a scintillation crystal, but uses no ultrasound imaging. The device is used externally on a patient, as the primary application is for the detection of tumors in lymph nodes.

U.S. Pat. No. 5,014,708 "Radioactive ray detecting therapeutic apparatus" discloses a "radioactive ray guided" therapeutic device, where in one embodiment, the delivered therapy comprises destroying target cells by ultrasound, and removal of the cells by aspiration.

U.S. Pat. No. 4,995,396 "Radioactive ray detecting endoscope" discloses an endoscope having both an ultrasonic imaging device and a radioactive ray (e.g., beta radiation) detecting device in the tip of the endoscope, but does not disclose use of a biopsy device.

U.S. Pat. No. 4,781,198 "Biopsy tracer needle" discloses a method and device for obtaining a tissue sample, comprising a biopsy tracer needle (i.e., containing a radiation source) guided to a target tissue by means of an external scintillation device. No use of ultrasound is disclosed.

U.S. Published Application No. 2007/0282221 "Ultrasound assist and X-ray assist biopsy devices" discloses a biopsy table, where a biopsy needle may be directed to a targeted tissue area by using an X-ray guided procedure for locating micro-calcifications, and using an ultrasound guided procedure for locating lesion masses.

What is needed is a probe, and more specifically a prostate endorectal probe, and an imaging system, and method of evaluating a target organ of a patient, which overcomes the shortcomings of the present state of the art.

BRIEF SUMMARY OF THE INVENTION

The present invention fulfills the long an unmet needs of the health care clinician in evaluating a target organ of a patient.

In one embodiment of this invention, a dual modality probe is provided comprising a housing having an external shell and an interior space, the housing having a first end, a middle section, and a second end, wherein the middle section is disposed between the first and the second ends, and wherein the second end is opposite the first end, an ultrasound sensor located within the first end of the interior of the housing, and a gamma probe sensor located within the first end of the interior of the housing and wherein the gamma probe sensor is located in juxtaposition to the ultrasound sensor within the interior of the housing. Preferably, this dual modality probe includes wherein the ultrasound sensor is disposed within the interior of the housing such that it is rotatable about a first axis of rotation, and/or wherein the gamma probe sensor is disposed within the interior of the housing such that it is rotatable about a second axis of rotation. This probe also includes an ultrasound transmit/receive element disposed in juxtaposition to and in communication with said ultrasound sensor. More preferably, the probe includes an electronic sensor positioning system located either on the exterior of the housing of the probe or within the interior of the housing for keeping track of the position of the probe and fusion of an image obtained from the ultrasound sensor and an image obtained from the gamma probe sensor, and wherein the electronic sensor positioning system is in communication with an outside computer processor for collecting data simultaneously from the gamma probe sensor, the gamma imaging detector, and the ultrasound sensor of the probe In another embodiment of this invention, the probe, as described herein, includes an external shield that has a first end and a second end that is disposed opposite the first end, the external shield having an interior section, the interior section having a diameter that accommodates the probe of this invention being inserted into the interior section of the external shield, and wherein at least one of the first end or second end of the external shield is open such that the housing of the probe is freely movable within and outside of at least a portion of the external shield. Preferably, the housing of this probe is movable for at least one of a lateral movement, a longitudinal movement, or a transverse movement within and outside at least a portion of the external shield. More preferably, the probe is in communication with a movement element for controlling the lateral, or longitudinal, or transverse movements of the probe within and outside at least a portion of the external shield.

In a preferred embodiment of this invention, the probe is provided, as described herein, including wherein the ultrasound sensor is placed in front of the gamma probe sensor within the housing of the probe.

In a less preferred embodiment of this invention, the probe is provided, as described herein, wherein the ultrasound sensor is placed behind the gamma probe sensor within the housing of the probe, and wherein the gamma probe sensor is placed in front of the ultrasound sensor within the housing of the probe.

In yet other embodiments of this invention, the probe, as described herein, includes wherein the ultrasound sensor and the gamma probe sensor are positioned on a support board within the housing of the probe.

Another embodiment of the dual modality probe of this invention, as described herein, includes a biopsy gun attached to the external shell of the housing of the probe, the biopsy gun equipped with a biopsy needle.

In another embodiment of this invention, a mobile dual modality imaging system is provided comprising a bed for accommodating a patient, an open rotating gantry mounted around the bed and mobile with respect to the bed, a gamma imaging detector secured to the rotating gantry above the bed and, optionally at least one separate gamma imaging detector secured to the rotating gantry below the bed, wherein each of the gamma imaging detectors are capable of angular rotation with respect to the bed to provide full angular projective sampling of a target organ of a patient lying on the bed, a probe (as described above, and herein) comprising at least an ultrasound sensor and a gamma probe sensor located in juxtaposition to each other, and an electronic sensor positioning system located either on the exterior of the housing of the probe or within the interior of the housing for keeping track of the position of the probe and fusion of an image obtained from the ultrasound sensor and an image obtained from the gamma probe sensor, the electronic sensor positioning system is in communication with an outside computer processor for collecting data simultaneously from the gamma probe sensor, the gamma imaging detector, and the ultrasound sensor of the probe.

In another embodiment of this invention, the imaging system, as described herein includes wherein the probe includes an ultrasound transmit/receive element disposed in juxtaposition to and in communication with the ultrasound sensor of the probe.

In a preferred embodiment of this invention, the dual modality imaging system, as described herein, includes the probe, as described herein, which further includes a gamma imaging detector electronics in communication with the gamma probe sensor.

Another embodiment of this invention provides for the imaging system, as described herein, wherein the gamma imaging detectors are capable of being operated in a static mode in which each of the detectors are fixed in position with respect to a target organ of a patient lying on the bed, or in a dynamic mode in which each of the detectors are rotated with respect to the target organ of the patient lying on the bed to provide full angular projective sampling of the target organ for enhanced 3D reconstruction, and wherein the detectors can be rotated to a new viewing angle with respect to the target organ and then operated in the static mode to better view the target organ of the patient lying on the bed and to optimize gamma ray spatial resolution. Preferably, the rotating gantry of the imaging system enables 360 degree angular sampling in a 3D imaging mode with the probe and the gamma imaging detectors. Most preferably, the dual modality imaging system as described herein includes wherein the ultrasound sensor is placed in front of the gamma probe sensor within the housing of the probe. In a less preferred embodiment of this invention, the dual modality imaging system includes the probe, as described herein, wherein the ultrasound sensor is placed behind the gamma probe sensor and wherein the gamma probe sensor is placed in front of the ultrasound sensor within the housing of the probe.

In another embodiment of this invention, the imaging system includes the probe, as described herein, having the ultrasound sensor and the gamma probes sensor of the probe positioned on a support board within the housing of the probe.

In yet another embodiment of this invention, the imaging system includes the probe, as described herein, wherein the ultrasound sensor is located in front of the gamma probe sensor within the housing of the probe, and the gamma probe sensor is positioned behind the ultrasound sensor within the housing of the probe, and wherein the ultrasound sensor is capable of being moved in and out of a forward position within the housing such that when the gamma probe sensor is actuated to produce at least one gamma ray, the gamma ray will pass through the housing of the probe and be unimpeded by the ultrasound sensor.

Another embodiment of this invention provides the imaging system, as described herein, including the probe, wherein the ultrasound sensor and the gamma probe sensor are placed in a fixed back-to-back arrangement with each other for forming a structure having the ultrasound sensor and the gamma probe sensor, and wherein the structure is rotatable about an axis of rotation from greater than zero degrees to 360 degrees within the housing of the probe.

Another embodiment of this invention provides for a method for evaluating a target organ of a patient. This method comprises injecting a patient with an imaging agent, providing a mobile dual modality imaging system, as described above and herein, and operating the dual modality imaging system such that said dual modality imaging system is positioned to scan a target organ of the patient. It will be appreciated that operating the dual modality imaging system includes inserting the probe of the imaging system into a cavity of the patient that is in proximity to the target organ under evaluation. For example, the probe of the imaging system is inserted into the rectum of a patient for evaluating rectal tissue of the colon or for evaluating the prostate gland of a male patient. The probe may be inserted into other body cavities of a patient for subsequent inspection thereof.

Another embodiment of the method of the present invention includes providing the imaging system with a probe, as described herein, having an optional biopsy gun positioned on the external shell of the housing of the probe for conducting a biopsy of the target organ.

The additional features and advantage of the disclosed invention is set forth in the detailed description which follows, and will be apparent to those skilled in the art from the description or recognized by practicing the invention as described, together with the claims and appended drawings.

BRIEF DESCRIPTIONS OF THE DRAWINGS

The foregoing aspects, uses, and advantages of the present invention will be more fully appreciated as the same becomes better understood from the following detailed description of the present invention when viewed in conjunction with the accompanying figures.

FIGS. 1A and 1B show the prostate dual modality endorectal probe (identified by numeral 10), of this invention, having an ultrasound sensor (identified by numeral 14) disposed at the forward end of the housing of the probe (10) and a gamma probe sensor (identified by numeral 12) within the housing of the probe (10) and located behind the ultrasound sensor (14). The probe (10) is inserted into the rectum of a male patient during an imaging phase of the method of the present invention. FIG. 1A specifically shows the probe during the US imaging phase. FIG. 1B specifically shows the probe during the gamma imaging.

Figure 13A:
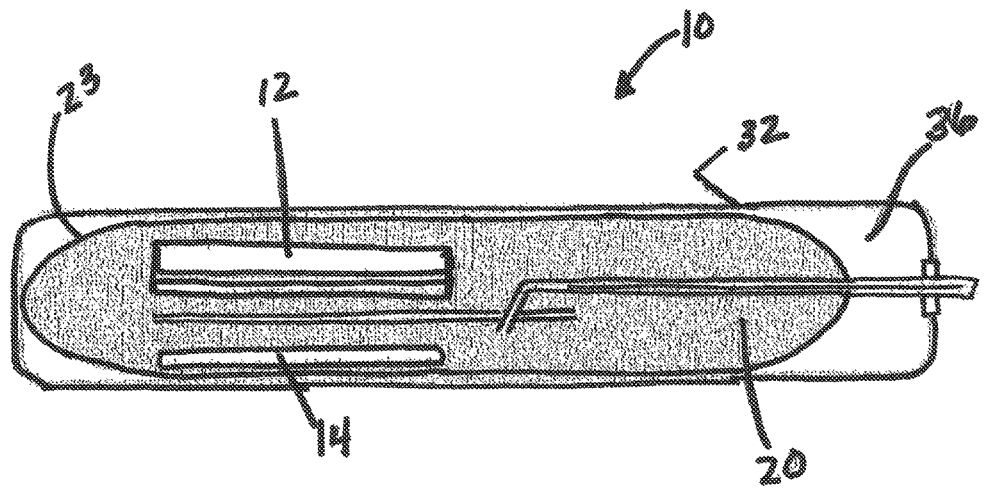
Figure 13B:
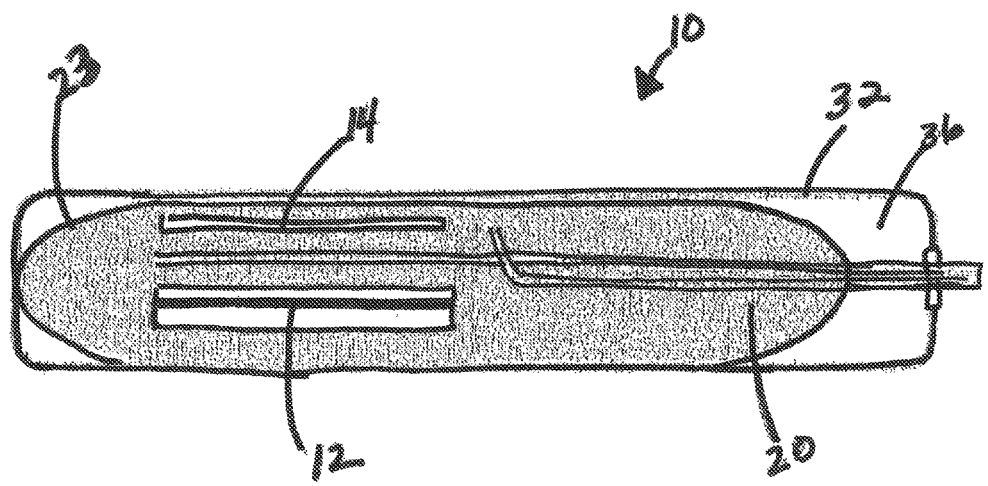

FIGS. 13A and 13B show an embodiment of the dual modality probe of the present invention wherein the probe (10) is rotated 180 degrees within the optional external shield (32). FIG. 13A shows the probe wherein the gamma probe sensor is in front of the ultrasound sensor 10. FIG. 13B show the orientation of the probe (10) within the external shield (32) after the probe (10) has been rotated 180 degrees within the external shield (32) resulting in the ultrasound probe (14) being positioned in front of the gamma probe sensor (14).

DETAILED DESCRIPTION OF THE INVENTION

The gamma probe sensor and ultrasound dual modality probe and dual modality imaging system of this invention provide significant improvement over existing devices and methods to obtain evaluations of a target organ of a patient, to perform a biopsy of the target organ, and to perform localized surgery of the target organ. The target organ may be, for example, but not limited to the prostate gland of a male patient, a gynecological anatomical structure of a female patient (vagina, cervix, uterus, etc.), or the rectum of a patient, or other anatomical structure of a patient wherein an endoscopic probe is utilized.

In a preferred embodiment of this invention, the probe and imaging system and method of this invention is useful to guide prostate biopsy/surgery with high resolution combined dual-modality gamma probe/US (Ultrasound) probe imaging in one compact endorectal device. The 2D images from the two modalities are naturally fused because the corresponding images are obtained at the same time and at the same probe position.

The probe and imaging system of the invention is a novel dedicated high resolution probe system. The ultrasound sensor element has enhanced ultrasound features allowing for prostate tissue differentiation in addition to its structural imaging and in addition to the molecular differentiation (of the cancerous from benign) tissues of the gamma probe sensor element. Combined spectroscopic power of these two modalities (Gamma ray/US) offers unique tissue differentiation. Optionally, the probe and imaging system of this invention include a probe, position and angle locator, as well as enhancements, described herein, to the basic operational parameters.

In a preferred embodiment of this invention, the method of the present invention utilizes the dual modality probe and the imaging system so that prostate biopsy can be performed accurately, which at the present time many of such biopsies of the prostate are poor at best.

The dual modality probe of this invention comprises in one housing both Ultrasound (US) and gamma probe sensor modalities. The imaging system comprises the probe of this invention, operating with an external single gamma imaging detector or a plurality of external gamma imaging detectors to provide the metabolic information related to the biological state of the target organ, such as for example, the prostate gland, and specifically about the presence of any cancerous structures exhibiting increased metabolic activity. In addition to cancer diagnosis, the dual-modality Gamma/US prostate probe and imaging system can be used in biopsy and in surgical guidance.

In one embodiment of this invention, a dual modality probe is provided comprising a housing having an external shell and an interior space, the housing having a first end, a middle section, and a second end, wherein the middle section is disposed between the first and the second ends, and wherein the second end is opposite the first end, an ultrasound sensor located within the first end of the interior of the housing, and a gamma probe sensor located within the first end of the interior of the housing and wherein the gamma probes sensor is located in juxtaposition to the ultrasound sensor within the interior of the housing. Preferably, the dual modality probe, as described herein, includes wherein the ultrasound sensor is disposed within the interior of the housing such that it is rotatable about a first axis of rotation, and/or wherein the gamma probes sensor is disposed within the interior of the housing such that it is rotatable about a second axis of rotation. The probe also includes an ultrasound transmit/receive element disposed in juxtaposition to and in communication with said ultrasound sensor. Preferably, the probe, as described herein, includes a gamma imaging detector electronics that is in communication with the gamma probe sensor. More preferably, the probe, as described herein, includes an electronic sensor positioning system located either on the exterior of the housing of the probe or within the interior of the housing, wherein the electronic sensor positioning system keeps track of the position of the probe and fusion of an image obtained from the ultrasound sensor and an image obtained from the gamma probe sensor, the electronic sensor positioning system is in communication with an outside computer processor for collecting data simultaneously from the gamma probe sensor, the gamma imaging detector, and the ultrasound sensor of the probe.

Another embodiment of this invention provides for the probe, as described herein, wherein the ultrasound sensor is located in front of the gamma probe sensor within the housing of the probe, and the gamma probe sensor is positioned behind the ultrasound sensor within the housing of the probe, and wherein the ultrasound sensor is capable of being moved in and out of a forward position within the housing such that when the gamma probe sensor is actuated to produce at least one gamma ray, the gamma ray will pass through the housing of the probe and be unimpeded by the ultrasound sensor Another embodiment of the dual modality probe of this invention, as described herein, includes wherein the ultrasound sensor and the gamma probe sensor are placed in a fixed back-to-back arrangement with each other for forming a structure having the ultrasound sensor and the gamma probe sensor, and wherein the structure is rotatable about an axis of rotation from greater than zero degrees to 360 degrees within the housing of the probe.

In another embodiment of this invention, the probe, as described herein, includes an external shield that has a first end and a second end that is disposed opposite the first end, the external shield having an interior section, the interior section of the external shield has a diameter that accommodates the probe of this invention being inserted into the interior section of the external shield, and wherein at least one of the first end or second end of the external shield is open such that the housing of the probe is freely movable within and outside of at least a portion of the external shield. Preferably, the housing of the probe of this invention, as described herein, is movable for at least one of a lateral movement, a longitudinal movement, or a transverse movement within and outside at least a portion of the external shield. More preferably, the probe is in communication with a movement element for controlling the lateral, or longitudinal, or transverse movements of the probe within and outside at least a portion of the external shield. The movement element may be for example but not limited to a mechanical stepper device as know by those persons skilled in the art, or a motorized unit that is controlled by a computer processor.

In a preferred embodiment of this invention, the probe is provided, as described herein, including wherein the ultrasound sensor is placed in front of the gamma probe sensor within the housing.

In a less preferred embodiment of this invention, the probe is provided, as described herein, wherein the ultrasound sensor is placed behind the gamma probes sensor within the housing.

In yet other embodiments of this invention, the probe, as described herein, includes wherein the ultrasound sensor and the gamma probe sensor are positioned on a support board within the housing of the probe.

Another embodiment of the dual modality probe of this invention, as described herein, includes a biopsy gun attached to the external shell of the housing of the probe, the biopsy gun equipped with a biopsy needle.

In another embodiment of this invention, a mobile dual modality imaging system is provided comprising a bed for accommodating a patient, an open rotating gantry mounted around the bed and mobile with respect to the bed, one or more gamma imaging detectors secured to the rotating gantry above the bed, and, optionally at least one separate gamma imaging detector secured to the rotating gantry below the bed, wherein each of the gamma imaging detectors are capable of angular rotation with respect to the bed to provide full angular projective sampling of a target organ of a patient lying on the bed, a probe comprising a housing having an external shell and an interior space, the housing having a first end, a middle section, and a second end, wherein the middle section is disposed between the first and the second ends, and wherein the second end is opposite the first end, an ultrasound sensor located within the first end of the interior of the housing, and a gamma probe sensor located within the first end of the interior of the housing and wherein the gamma probe sensor is located in juxtaposition to the ultrasound sensor within the interior of the housing, an electronic sensor positioning system located either on the exterior of the housing of the probe or within the interior of the housing, wherein the electronic positioning system keeps track of the position of the probe and fusion of an image obtained from the ultrasound sensor and an image obtained from the gamma probe sensor, the electronic sensor positioning system is in communication with an outside computer processor for collecting data simultaneously from the gamma probe sensor, the gamma imaging detector, and the ultrasound sensor of the probe. Preferably, the imaging system, as described herein, includes wherein the ultrasound sensor of the probe is disposed within the interior of the housing such that it is rotatable about a first axis of rotation. Preferably, the imaging system, as described herein, includes wherein the gamma probe sensor of the probe is disposed within the interior of the housing such that it is rotatable about a second axis of rotation. More preferably, the imaging system, as described herein, includes wherein the ultrasound sensor of the probe is disposed within the interior of the housing such that it is rotatable about a first axis of rotation and wherein the gamma probes sensor of the probe is disposed within the interior of the housing such that it is rotatable about a second axis of rotation. In another embodiment of this invention, the imaging system, as described herein includes wherein the probe includes an ultrasound transmit/receive element disposed in juxtaposition to and in communication with the ultrasound sensor of the probe.

In another embodiment of this invention, the imaging system includes the probe, as described herein, having the ultrasound sensor and the gamma probes sensor of the probe positioned on a support board within the housing of the probe.

Another embodiment of this invention provides for the imaging system, as described herein, wherein the gamma imaging detectors are capable of being operated in a static mode in which each of the gamma imaging detectors are fixed in position with respect to a target organ of a patient lying on the bed, or in a dynamic mode in which each of the gamma imaging detectors are rotated with respect to the target organ of the patient lying on the bed to provide full angular projective sampling of the target organ for enhanced 3D reconstruction, and wherein the gamma imaging detectors can be rotated to a new viewing angle with respect to the target organ and then operated in the static mode to better view the target organ of the patient lying on the bed and to optimize 3D spatial resolution. Preferably, the rotating gantry of the imaging system enables 360 degree angular sampling with the probe and the gamma imaging detectors.

Most preferably, the dual modality imaging system as described herein includes wherein the ultrasound sensor is placed in front of the gamma probe sensor within the housing of the probe. In a less preferred embodiment of this invention, the dual modality imaging system includes the probe, as described herein, wherein the ultrasound sensor is placed behind the gamma probes sensor within the housing of the probe.

In another embodiment of this invention, the imaging system includes the probe, as described herein, having the ultrasound sensor and the gamma probe sensor of the probe are positioned on a support board within the housing of the probe.

Another embodiment of this invention provides for a method for evaluating a target organ of a patient. This method comprises injecting a patient with an imaging agent, providing a mobile dual modality imaging system comprising a bed for accommodating a patient, an open rotating gantry mounted around the bed and mobile with respect to the bed, one or more of a gamma imaging detector secured to the rotating gantry above the bed, and, optionally at least one separate gamma imaging detector secured to the rotating gantry below the bed, wherein each of the gamma imaging detectors are capable of angular rotation with respect to the bed to provide full angular projective sampling of a target organ of a patient lying on the bed, a probe comprising a housing having an external shell and an interior space, the housing having a first end, a middle section, and a second end, wherein the middle section is disposed between the first and the second ends, and wherein the second end is opposite the first end, an ultrasound sensor located within the first end of the interior of the housing, and a gamma probe sensor located within the first end of the interior of the housing and wherein the gamma probe sensor is located in juxtaposition to the ultrasound sensor within the interior of the housing, an electronic sensor positioning system located either on the exterior of the housing of the probe or within the interior of the housing, wherein the electronic sensor positioning system is for keeping track of the position of the probe and fusion of an image obtained from the ultrasound sensor and an image obtained from the gamma probe sensor, the electronic sensor positioning system is in communication with an outside computer processor for collecting data simultaneously from the gamma probe sensor, the gamma imaging detector, and the ultrasound sensor of the probe, positioning the patient on the bed of the dual modality imaging system, and operating the dual modality imaging system such that said dual modality imaging system is positioned to scan a target organ of the patient. It will be appreciated that operating the dual modality imaging system includes inserting the probe of the imaging system into a cavity of the patient that is in proximity to the target organ under evaluation. For example, the probe of the imaging system is inserted into the rectum of a patient for evaluating rectal tissue of the colon or for evaluating the prostate gland of a male patient.

Another embodiment of the method of the present invention includes providing the imaging system with a probe, as described herein, having an optional biopsy gun positioned on the external shell of the housing of the probe for conducting a biopsy of the target organ.

It will be appreciated that the dual modality (hybrid) imaging prostate probe combining in one compact device the compact high resolution and high efficiency single gamma imager (probe sensor) with an ultrasound (US) sensor. The US component will typically provide not only the usual structural 3D information, as the standard TransRectal Ultrasound (TRUS) probe, but also the tissue differentiating information through proper US signal analysis, such as elastography. The mini gamma probe sensor will provide the direct metabolic information related to the biological state of the prostate and specifically about the presence of any cancerous structures exhibiting increased metabolic activity, when used with the single gamma labeled dedicated imaging agents for prostate cancer. In addition to cancer diagnosis, the dual-modality Gamma/US prostate probe of this invention can be used in biopsy and in surgical guidance.

The present invention provides a probe having a US modality in addition to a gamma probe sensor within the same compact enclosure, therefore eliminating the need for two separate probes, and providing a remedy to difficulties with co-registration of the two corresponding images from the two modalities when using separate probes. In addition, the signal analysis of the US signals will provide more detailed information on the mechanical properties of the prostate tissue, that will supplement the molecular information obtained with the gamma camera (probe sensor) and the dedicated prostate specific imaging agents that are know in the art. The US modality that we refer to here is therefore a "tissue-differentiating US" that has sensitivity to the type of tissue, for example if it is normal or abnormal. In case of prostate, the so called digital test is based on the urologist pressing the finger against the prostate (through the glove and the rectal wall) and trying to identify regions of hardened tissue. US is well adapted to replace the finger test and provides more accurate measurement of the elasticity of the tissue.

Before the prostate biopsy, the patient will be injected intravenously with the gamma imaging agent targeting the prostate cancer. During the procedure, the Gamma/US probe will be used to scan the region of the prostate for any signs of unusually high uptake of the gamma imaging agent, reflecting the presence of a potentially cancerous structure/lesion. US scan will provide an anatomical reference to the gamma image. The two 3D volumes of both modality images will be co-registered and fused to produce sets of any desired planar images of the tissue layers for definition where the hot spots/lesions are located. This in turn can provide guidance for biopsy and for surgery, if surgery is needed. If the patient undergoes surgery for a positive biopsy result, the prostate will be examined closely for correlation with the Gamma-US findings. In addition, the US probe can be equipped with enhanced US features or modalities, such as for example but not limited to, 3D operation, color and power Doppler, contrast-enhancement, harmonic and flash replenishment imaging, and elastography.

The dual modality Gamma/US probe and imaging system of the present invention can have also applications in gynecological exams and also in colon exams.

Figure 1A:
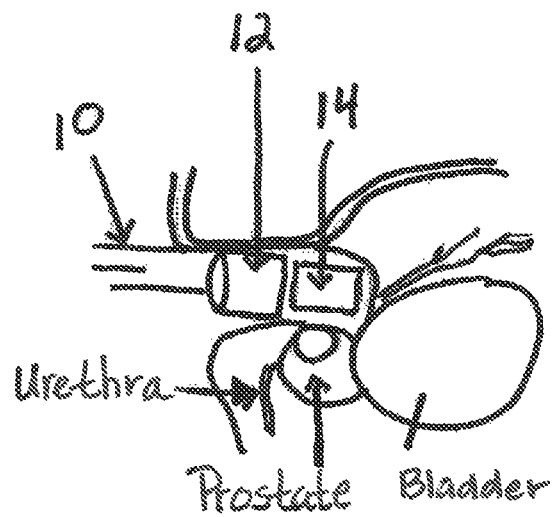
Figure 1B:
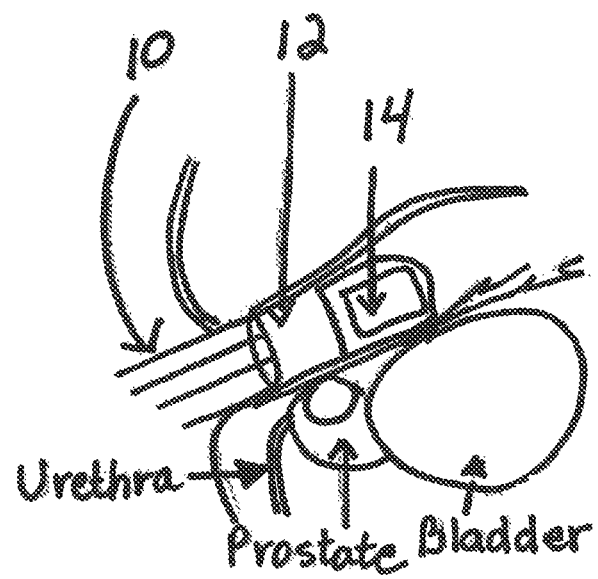

FIGS. 1A and 1B show a preferred embodiment of the dual-modality probe of the present invention inserted into the rectum of a patient for ultrasound imaging (US sensor placed in front of the gamma probe sensor within the probe housing). FIG. 1A shows the probe inserted into the rectum during the ultrasound imaging phase. By pushing the probe more inside the rectum (ie. further into the rectum) and changing the angle (FIG. 1B) the gamma probe sensor of the probe will come closer to the prostate gland for optimal gamma probe sensor imaging. Positioning a patient on his side and with the probe inserted into the rectum, the angle of the probe may be changed so that the ultrasound and gamma probe sensors can be better aligned with the prostate gland. It will be appreciated by those persons skilled in the art that FIGS. 1A and 1B shows the dual-modality probe with separate locations for the sensors, placed in two positions: FIG. 1A shows probe during the US imaging phase, and FIG. 1B shows the probe during the gamma imaging phase. The probe is maneuvered into position first with the US sensor close to the prostate, and then with the gamma sensor close to the prostate, respectively.

Figure 2:
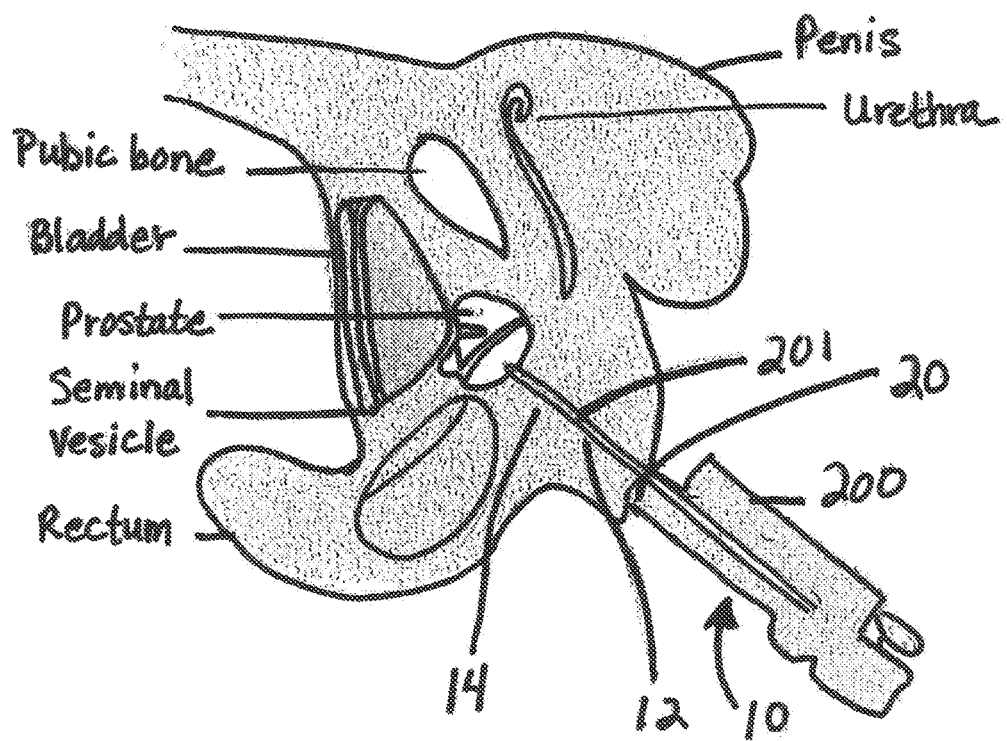
FIG. 2 shows an embodiment of the dual modality probe (10) of this invention wherein the ultrasound sensor (14) is placed in front of the gamma probe sensor (12) and the optional biopsy gun (200) with needle (201) attached to the external housing (20) of the probe (10). The probe (10) is shown inserted into the rectum of a male patient.

FIG. 2 shows a patient on his side with the probe inserted into the rectum. By changing angle of the probe, the ultrasound and gamma probe sensors can be better aligned with the prostate gland. FIG. 2 shows the dual modality probe (10) of this invention having a gamma probe sensor (12) and an ultrasound sensor (14). The probe (10) is equipped with an optional biopsy gun (200) equipped with a biopsy needle 9201) for performing a biopsy if after identifying suspicious lesions based upon the Gamma probe sensor/US results concerning elasticity characteristics. The ultrasound component (14) of the probe (10) will then be used to guide the needle of the biopsy gun based upon the established dual modality Gamma probe sensor/US scan of the target organ, here for example, the prostate gland.

Figure 3:
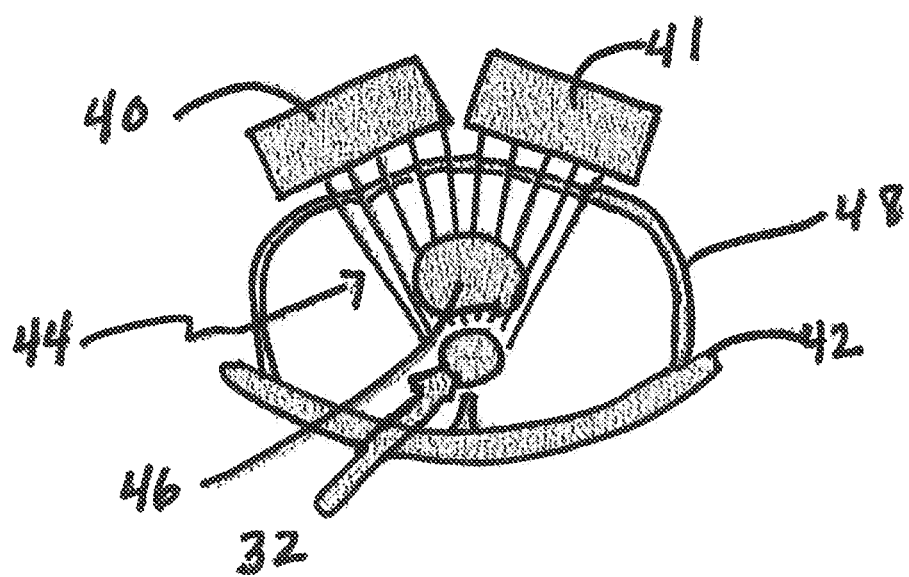
FIG. 3 is a cross-sectional view of an embodiment of the imaging system of the present invention showing the prostate endorectal probe operating in conjunction with two Gamma imaging detectors (41) placed stereotactically above the patient.

FIG. 3 shows another embodiment of the imaging system of the present invention including a first gamma imaging detector 40, an optional second gamma imaging detector 41, a bed 42 for the patient (48) to lie on, a gamma ray response signal 44, and the external shield 32 of the probe 10 (not shown) wherein the probe is inserted into the external shield 32. The patient's torso 48 and the prostate gland of a male patient 46 are also shown. FIG. 3 shows the external shield (32) that is inserted into the rectum of a patient and at least one gamma imaging detector (40 and 41) placed above the patient (48) lying on the bed (42) and operating in co-incidence with the gamma probe sensor element of the probe of this invention. Gamma response rays (44) are shown when the imaging system is operated. To immobilize the prostate (46) during the dual modality imaging system scan of this invention, the wall of the external shield (32) (having a larger diameter than the diameter of the probe of this invention) is used to immobilize the prostate during the whole imaging system procedure or method of the present invention. During the imaging system scan, the probe of this invention is moved inside the external shield longitudinally and transversely to cover the necessary volume of the prostate for both the ultrasound and the gamma scans.

Figure 4:
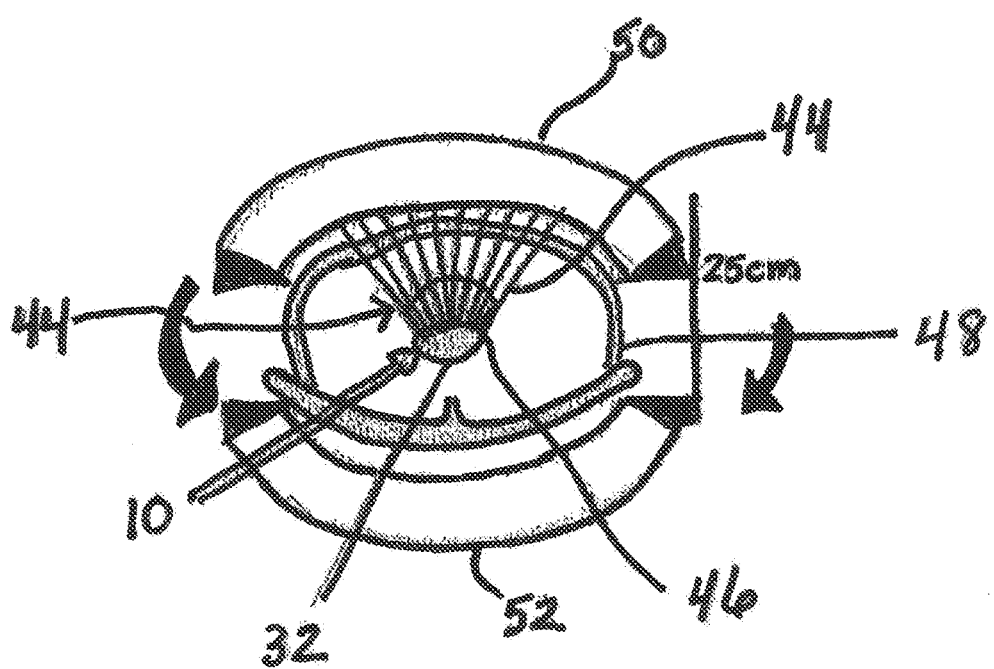
FIG. 4 is a cross-sectional view of an embodiment of the imaging system of the present invention showing the prostate endorectal probe operating in conjunction with upper gamma imaging detector (50), and optional lower gamma imaging detector (52).

FIG. 4 shows an optional embodiment of the imaging system of present invention wherein two gamma imaging detectors (50 and 52) are employed in the imaging system of this invention. One gamma imaging detector (50) secured to a gantry (not shown) is positioned above the patient (48) and a second gamma imaging detector (52) is secured to the same or another gantry positioned below the patient (48).

Figure 5:
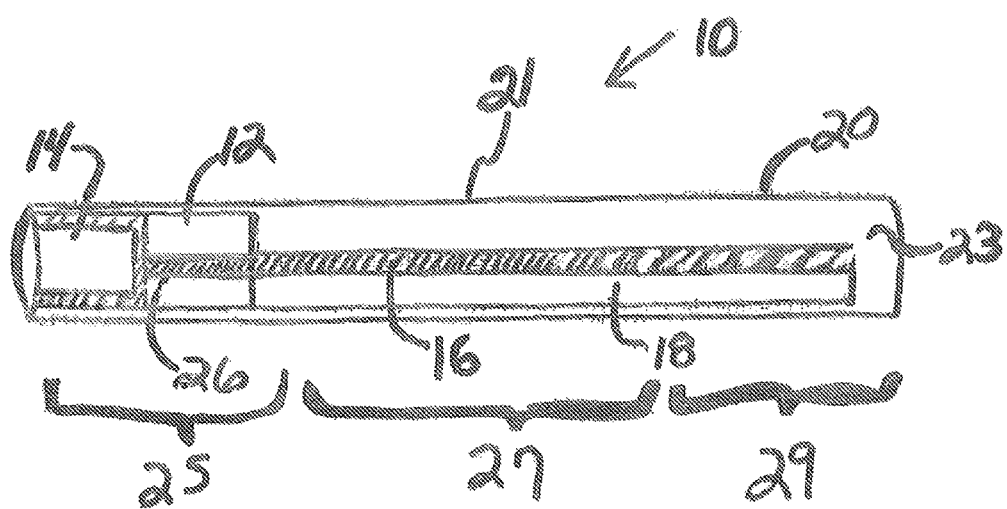
FIG. 5 shows a side view of the dual modality probe of the present invention wherein the ultrasound sensor is placed in front of the gamma probe sensor.
Figure 10:
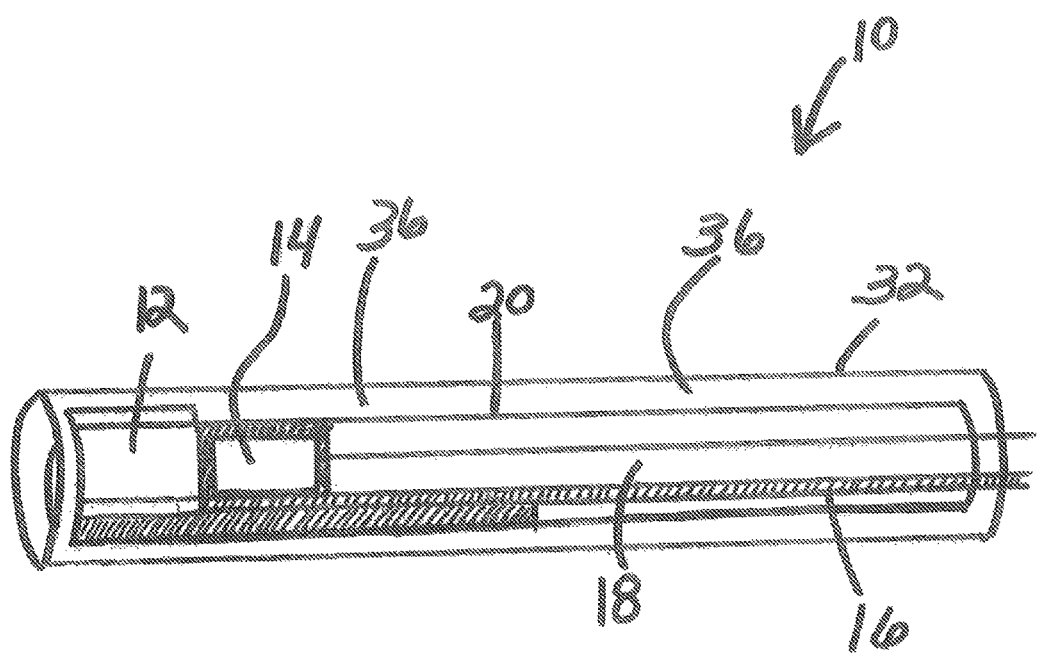
FIG. 10 is a side view of another embodiment of the probe of the present invention wherein the gamma probe sensor is placed in front of the ultrasound sensor of the probe.

FIG. 5 shows an embodiment of the dual modality probe 10 of the present invention. The probe 10 comprises a housing 20 having an external shell 21 and an interior space 23, the housing having a first end 25, a middle section 27, and a second end 29. The probe 10 has an ultrasound sensor 14, a gamma probe sensor 12, a substrate or support board 16, and a cable set 18 for providing electrical power to the gamma probe sensor 12 and the ultrasound sensor 14. The cable set 18 also includes a plurality of electrical conductors for transmitting signals between the gamma probe sensor 12, the ultrasound sensor 14, and one or more gamma imaging detectors (not shown). The probe 10 is in the configuration of an endorectal imaging probe 10 combining the molecular modality of the gamma probe sensor 12 with the structural modality of the ultrasound sensor 14 in a single housing (enclosure) 20. FIG. 10 shows the probe (10) having an external shield 32. Optionally, the probe 10 may have a probe shield (not shown) that partially or completely covers the probe 10 and is positioned between the housing 20 of the probe 10 and the external shield 32. An ultrasound coupling compound 36 may be placed between the housing 20 of the probe 10 and the external shield 32 (see FIGS. 10, 13A and 13B). As stated hereinbefore, the external shield 32 may be placed into the patient, and maintained in a relatively constant position. The gamma probe sensor 12 and the ultrasound sensor 14 may then be moved inside of the external shield 32 during the scanning and imaging procedure. The external shield 32 may thus function to exert a relatively constant and stable pressure on the prostate gland and surrounding tissue. This exertion of pressure enables the prostate endorectal probe 10 to substantially remain in position during an imaging scan. A software module (not shown) may provide advanced image and signal processing techniques for tissue classifications. Additional capabilities may provide for signal processing in the time domain, in the frequency domain, and in the wavelet domain, as is well known in the relevant art.

Figure 6:
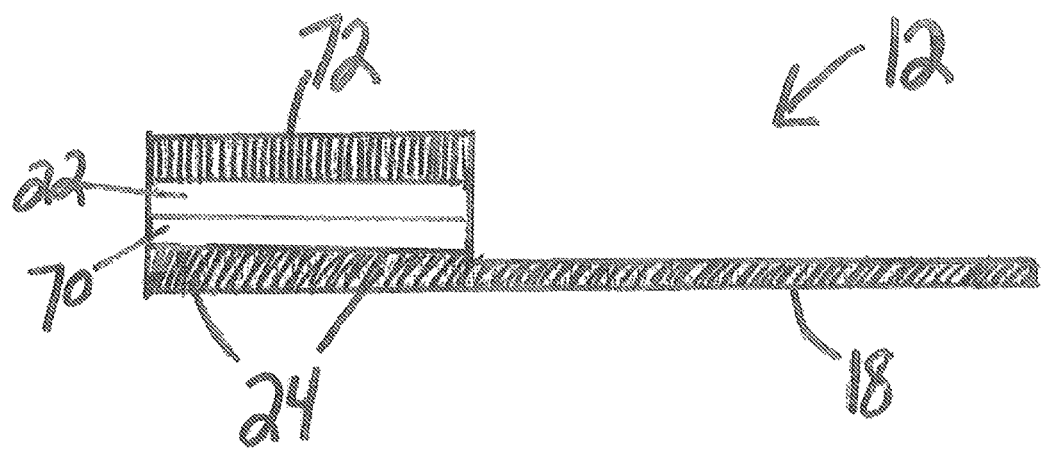
FIG. 6 shows a cross-sectional view of a gamma probe sensor.

FIG. 6 shows the collimator (72), scintillator ((22) and window (70) of the gamma probe sensor, and photodetector (24).

Figure 7:
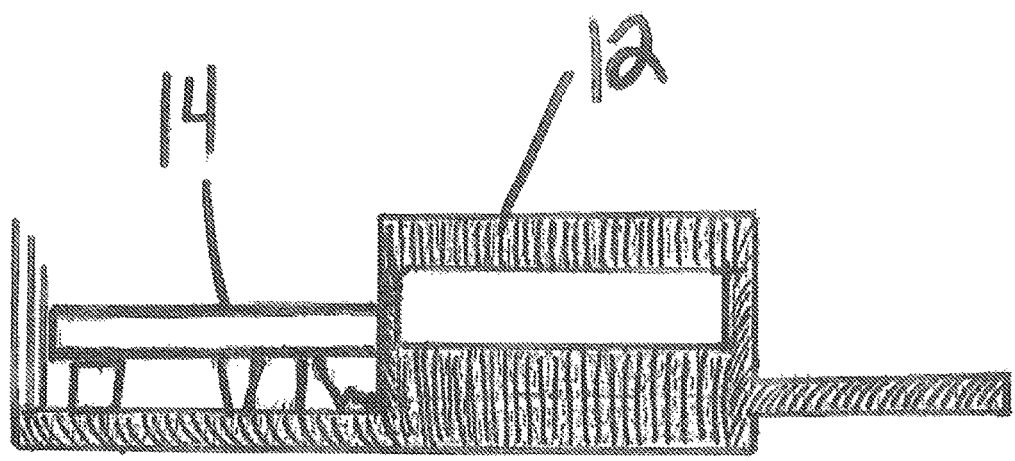
FIG. 7 shows a cross-sectional view of the gamma probe sensor of FIG. 6 wherein the gamma probe sensor is disposed adjacent an ultrasound sensor.

FIG. 7 shows the dual modality probe of the present invention wherein the US sensor is preferentially positioned in front of the gamma probe sensor of the device (probe 10), and with the gamma probe sensor positioned behind the ultrasound sensor. Positioning sensors (not shown) will keep a track of the probe position and enable fusion of the images obtained from the two modalities, ultrasound and gamma scans.

Figure 8:
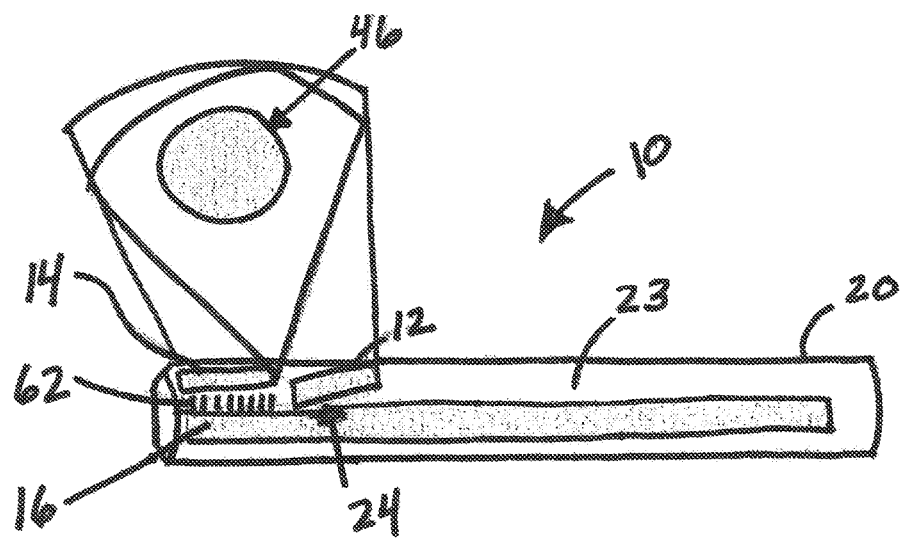
FIG. 8 is a side view of an embodiment of the probe of the present invention wherein the gamma probe sensor is disposed at an angle within the housing of the probe.
Figure 9:
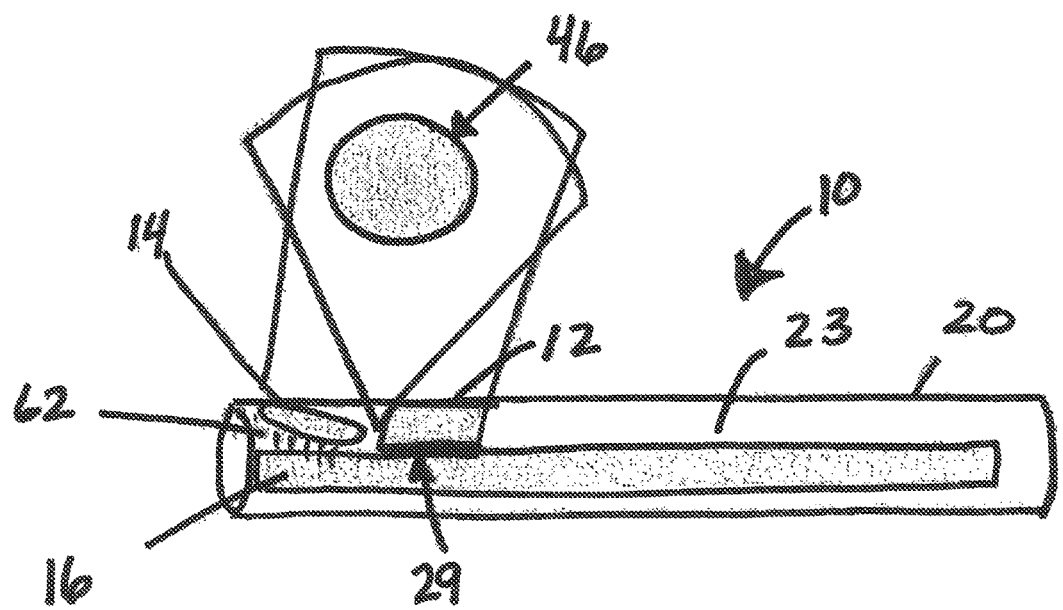
FIG. 9 is a side view of an embodiment of the probe of the present invention wherein the ultrasound sensor is disposed at an angle within the housing of the probe.

FIGS. 8 and 9 show other embodiments of the dual modality probe of the present invention with the optional external shield. The external shield is placed in the patient (rectum or other cavity) in a constant position at all times during the imaging system scan of this invention. The probe of this invention is inserted into the external shield and then the probe is moved inside the external shield during the scan and method of this invention. The presence of the external shield is exerting constant and stable pressure on the prostate and surrounding tissues and stabilizing the target organ and surrounding tissues during the method/scan of the present invention. In FIGS. 8 and 9, the gamma probe sensor element is placed behind the ultrasound sensor element. To assure proper transmission of the ultrasound waves/signal, application of proper coupling compound, such as for example, a gel, between the sensor and the external shield. In addition, there will need to be ultrasound coupling compound between the external shield and the patient's tissue. FIGS. 8 and 9 also show an embodiment of the present invention wherein the ultrasound sensor 14 comprises a two-dimensional piezoelectric crystals array 62 used to produce three-dimensional ultrasound images. In the configuration shown in FIGS. 8 and 9, the piezoelectric crystal array 62 may be immovably fixed to the substrate 16 (backing material). The substrate 16 and additional layers of substrate may be provided. In an exemplary embodiment, the ultrasound sensor 14 module 64 may operate at a frequency range of from about 2.50 MHz to about 15.0 MHz, with a field of view ranging from about 30.0 mm to about 150 mm. FIG. 8 shows the gamma probe sensor tilted within the interior 23 of the housing 20 of the probe 10. In yet another embodiment of the present invention, FIG. 9 shows the probe 10 of this invention wherein the ultrasound sensor 14 and the piezoelectric crystal array 62 are tilted within the interior 23 of the housing 20 of the probe 10. FIG.

9 shows that the ultrasound sensor 14 and the piezoelectric crystal array 62 may be rotated to more directly face the prostate gland 46 (or prostate cancer).

FIG. 10 shows a preferred embodiment of the dual-modality probe of this invention. The (thin) US sensor sits in front of the gamma sensor. In this configuration, the image fusion becomes greatly simplified as the two types of images (gamma and US) are obtained with the probe in the same position. Errors related to re-positioning of the probe necessary if the two images are taken at two different probe positions (as is the scenario with use of the background art devices), are entirely avoided with the probe and imaging system of this invention. Also, any movements of the prostate in-between the gamma and US measurements are avoided.

Figure 11:
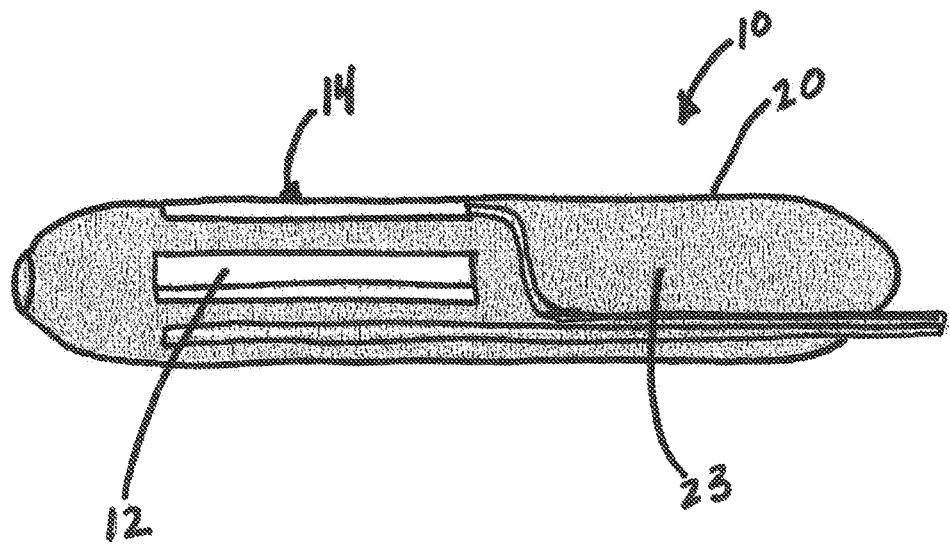
FIG. 11 is a side view of an embodiment of a probe of the present invention wherein the ultrasound sensor is placed in front of the gamma probe sensor.
Figure 12:
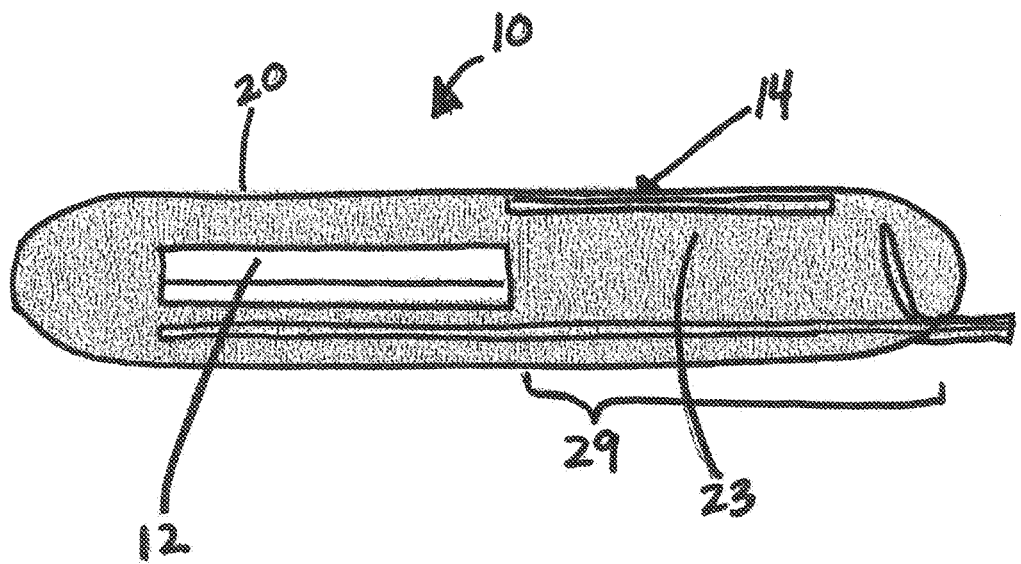
FIG. 12 is a side view of another embodiment of a probe of the present invention wherein the ultrasound sensor is moved (shifted backwards) into the second end (29) of the probe's (10) interior space (23) of the housing (20) of the probe (10) such that the ultrasound sensor (14) is out of the way of the gamma probe sensor (12).

The US sensor will absorb some fraction of the gammas (gamma rays) passing through the probe on a way to the gamma detector. This fraction of absorbed radiation is expected to be small. However, in the case if this becomes an issue, and in yet another implementation of the probe of the present invention, the US sensor element can be moved in and out of the position as shown in FIGS. 11 and 12. As shown in FIG. 11, the US images are acquired with the US sensor (14) in the forward position. Then, as shown in FIG. 12, with US sensor (14) shifted backwards into the interior (23) space of the housing (20) of the probe (10), the gamma images are acquired.

Another embodiment of the probe of this invention is shown in FIGS. 13A and 13B, that provides another solution to a problem in the case of high absorbance of the gammas (gamma radiation) passing through the US sensor (14). The gamma probe sensor (12) and US sensor (14) are placed back-to-back to each other and the probe (10) will be rotated inside the external shield (containment tube) (32) by 180 degrees between the two separate imaging sessions. With proper control of the procedure with proper mechanics and with on-board positioning sensors, and the steady maintained position of the external shield (32) (the external shield does not rotate), the two images of the gamma/US scans are easily co-registered. FIG. 13A shows the gamma probe sensor facing in the upward position (for example, near the target organ to be evaluated, such as the prostate gland-not shown), while in FIG. 13B, shows the probe after a 180 degree rotation within the external shield (32) wherein the US sensor (14) is turned towards (for example, near the target organ to be evaluated, such as the prostate gland—not shown).

Subsystems of the Disclosed Probe and Imaging System:

Ultrasound (US) element (emitter+receiver) with control/readout box and multi-parametrical analysis software Gamma sensor (collimator+scintillator+SiPM photodetector)

6 degrees of freedom (3 coordinates and 3 angles) positioning sensors with readout (two units for cross-check/backup)

Temperature sensor(s) with bias voltage feedback for the SiPMs in the gamma probe Fusion algorithms and software, fusing the PET and US modalities in 3D and in 2D projections for viewing and biopsy/surgery guidance Optional Subsystems and Features of the Disclosed Probe and Imaging System:

3D US operation

US elastography

US color and power Doppler, contrast-enhancement, harmonic and flash replenishment imaging, etc.

Pressure sensors on the outside of the probe (two positions] to assist with patient comfort Optical sensor (visible, UV, IR) with spectrum analyzer The preferred technology of the gamma probe is a combination of compact Silicon Photomultipliers (SiPMs) and pixellated or plate scintillators. The scintillators detect the gammas from gamma emissions of the radioactive label in the prostate and its surroundings. With the collimator (See FIG. 6, element identified by numeral 72) installed in front of the scintillator (See FIG. 6, element identified by numeral 22), only a high fraction of the directional gamma rays that went through the collimator are detected in the scintillator and convert their detected energy into scintillation signals, that are in turn detected in the SiPM photodetectors. Signal processing of individual pads of the pad array constituting SiPMs, and subsequent center-of-gravity position calculating algorithm, provide localization of the scintillation light flashes and therefore the localization of the initial entry points of the gamma rays. A large enough accumulation of detected gamma events provides a distribution (image) of the gamma emission points in the screened section of the prostate.

In the simplest case, the US sensor can be the standard 2D US sensor that is well known in the art, and may be used in guiding prostate biopsies, such as Model BK Medical 8808. However, the preferred ultrasound probe comprises a 2D array of piezoelectric material that provides 3D ultrasound images. The typical high performance probe will operate at a frequency range from 2.5 MHz up to 15 MHz. The field of view can easily have a range from 30 mm to 150 mm. The 2D piezoelectric array is diced into pillars to generate ultrasound beams. The probe will also consist of a backing layer and two matching layers to broaden the frequency spectrum and therefore improve the image resolution. The 2D array probe will be able to steer in different angles to generate ultrasound beams along different directions. The field of view ranging from 30 mm to 150 mm can be controlled by clinicians to image a specific region of interest (ROI) of a target organ. Additionally, this ultrasound technology will be equipped with B-mode, M-mode, and color Doppler techniques to ease interpretation of ultrasound images and provide information on blood flow circulations.

Advanced image and signal processing techniques for tissue classification will be typically implemented on radiofrequency echoes obtained from the normal and cancer prostate tissue. Signal processing analyses in time-, frequency-, and wavelet-domains can be performed to detect tissue abnormalities of prostate tissue to differentiate cancer.

The two modalities (gamma/US) can operate separately, but the preferred operation is with 3D ultrasound images extracted and fused with gamma images for enhanced tissue visualization and differentiation.

Construction of the Gamma Sensor

The following is a preferred construction of the gamma probe sensor. The preferred scintillator materials (in the form of plates or arrays) due to their compactness and high light output are: CsI(Tl), CsI(Na), and GSO. Other scintillators such NaI(Tl), LaBr3, that need air-tight envelopes, can also be used.

Tungsten composite collimator technology from Mikro Systems. High granularity of the produced structures well matches the high resolution of the scintillation sensor Preferably, a buttable arrangement of four Hamamatsu monolithic SMD arrays are employed. After redirecting by 180 degrees two left cables from the structure and adding a scintillator and a collimator, a ~1" gamma detection module is obtained. Two of these modules can be stacked one behind the other to form a larger ~1"×2" module, but with a small gap and step in between. An external gamma shield needs to be added to prevent gamma radiation to bypass the collimator and enter the scintillator from the sides and the back of the probe. By using only one column of SMD arrays, used as building blocks, a narrower and more patient friendly probe will be obtained, ~½"×1-2" in size. Transversal scanning and/or tilting the module can be used to cover the whole prostate region In another embodiment, the gamma sensor includes a scintillation/collimator package, where the scintillator elements (CsI(TI) or CsI(Na)) are imbedded in the collimator structure. Collimator septa function in this case also as separating walls of the individual scintillator pixels. To optimize the scintillation light transmission and collection, the surface of the septa is covered with reflective white material/paint. This design permits the most compact (in vertical dimension) structure of the collimator/scintillator package. Mikro Systems is one of the companies custom-making such structures Laboratory validation of the gamma probe sensor of the new design has been achieved. First, the monolithic Hamamatsu SiPM, Model MPPC-MAl-l(X), was coupled through a 2 mm thick light spreader window to a 1 mm step 3 mm thick CsI(TI) array from Hilger Crystals, UK. Then, we tested the 1.2 mm step CsI(T13 array imbedded in the collimator, also coupled through a 2 mm window, and using optical grease between all optical surfaces. Finally, a 1 mm thick 20 mm×20 mm GSO plate was also tested. The advantage of the latter design using plate GSO is that the whole structure becomes very compact, benefiting from high stopping power of GSO.

16ch tight MPPC array MPPC-MAl-l(X) from Hamamatsu is in a mounting frame. The pad step is ~3 mm. The array is mounted on a PC board with amplifiers, from AiT.

Results were obtained with the 1 mm step 3 mm thick CslfTI) scintillation array tested with the Co57 source (122 keV gammas) The array is made out of several joined sections that produce observed discontinuities in the images. The CsI(TI) array was coupled to the monolithic MPPC array from Hamamatsu via a 2 mm spreader window. Dry coupling was used. Raw image and vertical profile through one of the pixel columns, demonstrate sub-mm intrinsic spatial resolution. The energy spectrum from one of the 1×1×3 mm CsI(TI) pixels shows scattered radiation peak and photopeak with energy resolution 19.5% FWHM @122 keV.

Results were obtained with the same 1 mm step 3 mm thick CsI(TI) scintillation array and wet (optical grease) coupling. Raw image and vertical profile through one of the pixel columns, confirm sub-mm intrinsic spatial resolution. The energy spectrum from one of the 1×1×3 mm CsI(TI) pixels shows scattered radiation peak and 122 keV photopeak with energy resolution 18.6% FWHM.

Results were obtained with the 1.2 mm step 3 mm thick CsI(Na) scintillation array tested with the Co57 source. The array was coupled to the monolithic MPPC array from Hamamatsu via a 2 mm spreader window. Wet (optical grease) coupling was used. Raw image and profile through one of the pixel rows, again demonstrate sub-mm intrinsic spatial resolution.

Results were obtained with the 1 mm thick GSO scintillator plate tested with the Co57 source. The plate was coupled to the monolithic MPPC array from Hamamatsu via a 2 mm spreader window. Wet coupling was used. Raw image of a 1 mm thick lead masks having an array of 1 mm diameter holes, spaced at 2 mm center-to-center. Vertical profile through one of the columns demonstrates sub-mm intrinsic resolution of this solution. Overall energy resolution (no region selection) of 36% @122 keV was measured.

The above pilot results demonstrate that compact gamma imaging probes based on SiPMs and scintillators for prostate imaging applications with 1 mm intrinsic resolution are feasible, and the overall spatial resolution (and sensitivity) will be defined by the collimator design and geometry of the distance to lesion. The composite tungsten collimators are available from Mikro Systems in Charlottesville, Va.

It will be understood from the description provided herein and the attached figures, that the present invention provides a hybrid imaging dual modality probe and imaging system (device) that functions to provide accurate localization of a target tumor or organ. The dual modality probe includes an ultrasound component to provide structural 3-D information related to the target tumor or organ, and a gamma probe sensor component to provide metabolic information related to the biological state of the target tumor or organ. In particular, when used to image the prostate gland of a male patient, the dual modality imaging system of this invention may be used to specifically detect the presence of cancerous structures in the prostate, and may be adapted to identify cancerous structures showing increased metabolic activity. The imaging information obtained by using the present dual modality imaging system may be used to provide guidance for a biopsy procedure, for example, or for other medical procedures requiring surgical intervention.

Those persons skilled in the art will understand that changes could be made to the embodiments described above without departing from the inventive concept of the probe, the imaging system, and methods of the present invention. The accompanying drawings are included to provide a further understanding of various features and embodiments of the probe, imaging system, and methods of the invention which, together with their description serve to explain the principles and operation of the invention set forth herein. It is understood, therefore, that this invention is not limited to the particular embodiments disclosed, but is intended to cover modifications that are within the spirit and scope of the invention, as defined by the appended claims.

We claim:

1. A dual modality probe comprising:
   a housing having an external shell and an interior space, said housing having a first end, a middle section, and a second end, wherein said middle section is disposed between said first and said second ends, and wherein said second end is opposite said first end;
   an ultrasound sensor located within the first end of said interior of said housing; and
   a gamma probe sensor located within said first end of said interior of said housing and wherein said gamma probe sensor is located in juxtaposition to said ultrasound sensor within said interior of said housing, wherein said gamma probe sensor having a first diameter and said ultrasound sensor having a second diameter, and said external shell of said housing having a third diameter, said first diameter of said gamma probe and said second diameter of said ultrasound sensor each having a circumference smaller than a circumference of said third diameter of said external shell of said housing, and including wherein said ultrasound sensor of said probe is disposed within said interior of said housing such that it is rotatable about a first axis of rotation and wherein said gamma probe sensor of said probe is disposed within said interior of said housing such that it is rotatable about a second axis of rotation.

2. The dual modality probe of claim 1 including an ultrasound transmit/receive element disposed in juxtaposition to and in communication with said ultrasound sensor.

3. The dual modality probe of claim 1 including a gamma imaging detector electronics in communication with the gamma probe sensor.

4. The dual modality probe of claim 1 including an electronic sensor positioning system located either on said exterior of said housing of said probe or within said interior of said housing for keeping track of the position of the probe and fusion of an image obtained from said ultrasound sensor and an image obtained from said gamma probe sensor, said electronic sensor positioning system is in communication with an outside computer processor.

5. The dual modality probe of claim 1 including an external shield that has a first end and a second end that is disposed opposite said first end, said external shield having an interior section, said interior section having a diameter that accommodates said probe to be inserted into the interior section of said external shield, and wherein at least one of said first end or second end of said shield is open such that said housing of said probe is freely movable within and outside of at least a portion of said external shield.

6. The dual modality probe of claim 5 including wherein said housing of said probe is in communication with a movement element for controlling at least one of a lateral movement, or a longitudinal movement, or a transverse movement of said probe within and outside at least a portion of said external shield.

7. The dual modality probe of claim 1 wherein said ultrasound sensor is placed in front of said gamma probe sensor within said housing.

8. The dual modality probe of claim 1 wherein said ultrasound sensor is placed behind said gamma probe sensor within said housing.

9. The dual modality probe of claim 7, wherein said ultrasound sensor is located in front of said gamma probe sensor within said housing of said probe and said gamma probe sensor is positioned behind said ultrasound sensor within said housing of said probe, and wherein said ultrasound sensor is capable of being moved in and out of a forward position within said housing such that when said gamma probe sensor is actuated to produce at least one gamma ray, said gamma ray will pass through said housing of said probe and be unimpeded by said ultrasound sensor.

10. The dual modality probe of claim 1 wherein said ultrasound sensor and said gamma probe sensor are positioned on a support board within said housing.

11. The dual modality probe of claim 1 wherein said ultrasound sensor and said gamma probe sensor are placed in a fixed back-to-back arrangement with each other for forming a structure having said ultrasound sensor and said gamma probe sensor, and wherein said structure is rotatable about an axis of rotation from greater than zero degrees to 360 degrees within said housing of said probe.

12. The dual modality probe of claim 1 including a biopsy gun attached to the external shell of said housing of said probe, said biopsy gun equipped with a biopsy needle.

* * * * *